United States Patent [19]

Bos et al.

[11] Patent Number: 4,871,838

[45] Date of Patent: Oct. 3, 1989

[54] PROBES AND METHODS FOR DETECTING ACTIVATED RAS ONCOGENES

[75] Inventors: Johannes L. Bos, Leiden; Alex J. Van der Eb, Oegstgeest, both of Netherlands

[73] Assignee: The Board of Rijks Universiteit Leiden, Leiden, Netherlands

[21] Appl. No.: 758,104

[22] Filed: Jul. 23, 1985

[51] Int. Cl.$^4$ .................... C07H 21/00; C12Q 1/68
[52] U.S. Cl. ........................................ 536/27; 935/78; 935/9; 435/6; 435/803; 436/813
[58] Field of Search ............................... 435/6, 803, 91; 436/501, 813, 63, 94; 536/27; 935/78, 9

[56] References Cited

U.S. PATENT DOCUMENTS 4,535,058 8/1985 Weinberg et al. ............... 935/77 X
4,725,550 2/1988 Perucho et al. ................ 536/27 X

OTHER PUBLICATIONS

Guerrero, I. et al., *Science*, vol. 225, 1984, pp. 1159–1162.
Zarbl, H. et al., *Nature*, vol. 315, 1985, pp. 382–385.
Guerrero, I. et al., *Proc. Natl. Acad. Sci. USA*, vol 81, 1984, pp. 202–205.
Studencki, A. B. et al., *DNA*, vol. 3, 1984, pp. 7–15.

*Primary Examiner*—Johnnie R. Brown
*Assistant Examiner*—Jeremy M. Jay
*Attorney, Agent, or Firm*—John P. White

[57] ABSTRACT

Molecules complementary to nucleotide sequences encoding mutant ras protiens which contain a single-base mutation in the codon encoding amino acids at position 13, 12 or 61 have been produced. These molecules are useful in methods of detecting specific single-base mutations in altered ras genes and the specific cancers associated with such mutations.

7 Claims, 2 Drawing Sheets

Figure 1

```
                           61
N-ras     ----ACA GCT GGA CAA GAA GAG TA----

N61-I         ACA GCT GGA CAA GAA GAG TA

N61-II        ACA GCT GGA  AA GAA GAG TA
                           G
                           A
                           T

N61-III       ACA GCT GGA C A GAA GAG TA
                           G
                           C
                           T

N61-IV        ACA GCT GGA CA  GAA GAG TA
                             C
                             T
```

Figure 2

```
                          13 12
N12-wt     5' TTCCCAACACCACCTGCTCC 3'

N12-p1        TTCCCAACACCAC TGCTCC
                           G
                           A
                           T

N12-p2        TTCCCAACACCA CTGCTCC
                          G
                          A
                          T

N13-p1        TTCCCAACAC ACCTGCTCC
                        G
                        A
                        T

N13-p2        TTCCCAACA CACCTGCTCC
                       G
                       A
                       T

61
N61-wt     5' ACACCTGGACAAGAAGACTA 3'
```

PROBES AND METHODS FOR DETECTING ACTIVATED RAS ONCOGENES

BACKGROUND OF THE INVENTION

Throughout this application various publications are referenced by numbers within parentheses. Full citations for these publications may be found at the end of the specification immediately preceding the claims. The disclosures of these publications in their entireties are hereby incorporated by reference into this application in order to more fully describe the state of the art to which this invention pertains.

The human gene family consists of three members: the H-ras, K-ras and the N-ras gene (1) These genes code for related proteins of 21kD, which are located at the inner face of the cell membrane (36) and are thought to be involved in transducing signals from cell surface receptors to their intracellular targets (37). A significant portion of tumor cell lines and fresh tumor tissue has been found to possess an activated ras gene. Such genes are characterized by their ability to induce oncogenic transformation of mouse 3T3 cells. In most cases so far analyzed the activation is due to a point mutation in the 12th or 61st codon of a ras gene resulting in a single amino acid substitution in the gene product (3-15).

The fixed position of the mutations makes it possible to use synthetic oligonucleotides to screen directly for the presence of activating mutations in genomic DNA of tumor tissue. This direct assay is based on the fact that a fully matched DNA hybrid has a higher thermal stability than a hybrid with a mismatched base-pair. By using a selective washing procedure nonperfect hybrids can melt off, whereas a fully matched hybrid remains stable.

This type of assay has been introduced by Conner et al. (24) to detect a single base mutation in the beta globin gene. In a previous study, differential hybridization with synthetic oligonucleotides has been used to detect point mutations induced by chemical carcinogens in codon 12 of Ha -ras −1 in rat DNA (44). Similarly, this approach has been used to demonstrate a single base change in the mouse K -ras oncogene in codon 12 in tumors induced by gamma radiation (45). To detect possible mutations that lead to amino acid substitution at position 12 or 61 of the three ras genes, H ras, K-ras and N-ras, we have synthesized sets of 20-mers which can detect whether and at which position a mutation is present. One embodiment of this invention concerns an assay system for mutations in codon 12 and 61 of the human ras gene.

The use of focus assays to detect morphological transformation of NIH 3T3 cells in DNA transfection experiments has shown that between 10–30% of human tumors contain altered forms of either the c-H-ras-1 gene, the c-K-ras-2 gene or the N-ras gene. These genes encode GTP binding proteins of 188 and 189 amino acids which are located at the inner surface of the cell membrane and are highly conserved in evolution (1,2). In 15 or so cases of altered genes in human tumors or in human tumor cell lines that have been analyzed so far, activation has been shown to be the result of a single basepair mutation which leads to the substitution of either glycine at amino acid position 12 or glutamine at position 61 (3–17). However, recent in vitro mutagenesis experiments indicated that mutations at amino acids 13, 59, and 63 can also lead to transforming activity (18).

We have studied the presence of activated ras genes in Acute myeloid leukemia (AML). This leukemia is characterized by abnormal proliferation and differentiation of cells of the myeloid, monocytic and erythroid lineage. It is subdivided in 6 groups, FAB M1–M6, (19) depending on which immature cell is dominant in population. Using a direct in vivo selection assay in nude mice of transfected 3T3 cells (20) we have found that 4 out of 5 AML DNAs tested contain an activated gene. An altered N-ras oncogene was also detected in another AML sample using the focus formation assay. These activated N-ras genes were analyzed for the presence of mutations using a set of synthetic oligonucleotide probes and it was found that all 5 activated N-ras genes contain a mutation at codon 13. One embodiment of this invention concerns the use of these oligonucleotide probes to detect a mutation at codon 13 of the N-ras gene. Detection of such a mutation is useful in the diagnosis of certain types of AML and other tumors.

SUMMARY OF THE INVENTION

Molecules useful as probes for detecting in DNA which encodes a ras-protein a mutation in a codon resulting in a different amino acid being translated into the protein than the amino acid encoded for prior to mutation have been produced. These molecules comprise a nucleotide sequence of at least 12 but not more than 43 nucleotides having the formula from 5' to 3' B -Q-D. B is a nucleotide sequence of from 0 to about 20 nucleotides complementary to a DNA sequence present in the DNA which encodes the ras protein, the DNA sequence to which B is complementary encoding amino acids at the amino terminal side of the amino acid encoded by the codon in which the mutation is present. D is a nucleotide sequence of from 0 to about 20 nucleotides complementary to a DNA sequence present in the DNA which encodes the ras protein, the DNA sequence to which D is complementary encoding amino acids at the carboxyl terminal side of the amino acid encoded by the codon in which the mutation is present. Q is a nucleotide sequence of 3 nucleotides complementary to a sequence which encodes the amino acid at the position of the mutation and which contains a single-base pair mutation.

The invention concerns both DNA and RNA molecules and molecules complementary to these molecules.

The molecules of the invention may be labeled with detectable moieties and used in methods of detecting activated ras oncogenes which contain single-base mutations in the codons encoding positions 12, 13 or 61.

The methods of detecting an activated ras gene containing a single-base mutation comprise cleaving a human subject's genomic DNA with an appropriate restriction enzyme or enzymes under suitable conditions to produce DNA fragments. The resulting fragments are then treated to obtain single-stranded DNA molecules. The single-stranded DNA molecules so obtained are contacted with one of the DNA molecules of this invention under suitable conditions permitting hybridization of complementary molecules. The hybridized molecules are treated under suitable conditions permitting only fully complementary molecules to remain hybridized and causing imperfectly hybridized molecules to separate. The presence of the fully hybridized molecules is detected and thereby the single-base mutation in the activated ras gene is also detected.

Another embodiment of the invention concerns methods of detecting an activated ras gene which contains a single base mutation in the codon encoding a specific amino acid by detecting the altered ras-protein product of the mutated gene with monoclonal antibodies.

DETAILED DESCRIPTION OF THE INVENTION

Molecules useful as probes for detecting in DNA which encodes a ras-protein a mutation in a codon resulting in a different amino acid being translated into the protein than the amino acid encoded for prior to the mutation have been produced. These molecules comprise a nucleotide sequence of at least 12 but not more than 43 nucleotides having the formula from 5' to 3' B -Q-D.

B is a nucleotide sequence of from 0 to about 20 nucleotides complementary to a DNA sequence present in the DNA which encodes the ras protein, the DNA sequence to which B is complementary encoding amino acids at the amino terminal side of the amino acid encoded by the codon in which the mutation is present. D is a nucleotide sequence of from 0 to about 20 nucleotides complementary to a DNA sequence present in the DNA which encodes the ras protein, the DNA sequence to which D is complementary encoding amino acids at the carboxyl terminal side of the amino acid encoded by the codon in which the mutation is present. Q is a nucleotide sequence of 3 nucleotides complementary to a sequence which encodes the amino acid at the position of the mutation and which contains a single-base pair mutation.

The invention also concerns molecules which are complementary to the molecules described above. The molecules of the invention can be DNA or RNA molecules.

Certain embodiments of the invention concern molecules useful as probes for single base mutations in the codons encoding the amino acids at position 12, 13 or 61 of a ras protein.

A specific embodiment of the invention concerns a molecule useful as a probe for detecting in DNA which encodes the N-ras protein a mutation in the codon at position 13 of the N-ras gene resulting in a different amino acid being translated into the protein than the amino acid encoded for prior to the mutation. This molecule comprises a nucleotide sequence of at least 12 but not more than 43 nucleotides having the formula from 5' to 3' B-Q-D.

B is a nucleotide sequence of from 0 to about 20 nucleotides complementary to a DNA sequence present in the DNA which encodes the N-ras protein, the DNA sequence to which B is complementary encoding amino acids at the amino terminal side of the amino acid encoded at position 13 of the N-ras gene. D is a nucleotide sequence of from 0 to about 20 nucleotides complementary to a DNA sequence present in the DNA which encodes the N-ras protein, the DNA sequence to which D is complementary encoding amino acids at the carboxyl terminal side of the amino acid encoded at position 13 of the gene. Q is a nucleotide sequence of 3 nucleotides complementary to a DNA sequence which encodes an amino acid other than glycine.

The codon Q in this embodiment can be either ACG, ACA, ACT, AGC, AAC or ATC, and the complete sequence of a 20 mer embodiment of the invention is TTCCCAACACGACCTGCTCC, TTCCCAACACAACCTGCTCC, TTCCCAACACTACCTGCTCC, TTCCCAACAGCACCTGCTCC, TTCCCAACAACACCTGCTCC, or TTCCCAACATCACCTGCTCC.

A molecule complementary to a nucleotide sequence encoding a mutant N-ras protein which contains a single base pair mutation in the codon encoding the amino acid at position 12 has also been produced. The nucleotide sequence of this 20 mer molecule comprises TTCCCAACACCACGTGCTCC, TTCCCAACACCACATGCTCC, TTCCCAACACCACTTGCTCC, TTCCCAACACCAGCTGCTCC, TTCCCAACACCATCTGCTCC, or TTCCCAACACCAACTGCTCC.

Another embodiment of the invention concerns molecules complementary to a nucleotide sequence encoding a mutant N-ras protein which contains a single base pair mutation in the codon encoding the amino acid at position 61. The nucleotide sequence of this DNA molecule comprises ACAGCTGGAGAAGAAGAGTA, ACAGCTGGAAAAGAAGAGTA, ACAGCTGGATAAGAAGAGTA, ACAGCTGGACGAGAAGAGTA, ACAGCTGGACCAGAAGAGTA, ACAGCTGGACTAGAAGAGTA, ACAGCTGGACACGAAGAGTA or ACAGCTGGACATGAAGAGTA.

Another embodiment of the invention concerns molecules useful as probes for an altered K-ras gene. Molecules complementary to a DNA sequence encoding a mutant K-ras protein which contains a single base pair mutation in the codon encoding the amino acid at position 12 have been synthesized. The nucleotide sequence of these molecules comprises GTTGGAGCTAGTGGCGTAGG, GTTGGAGCTTGTGGCGTAGG, GTTGGAGCTCGTGGCGTAGG, GTTGGAGCTGTTGGCGTAGG, GTTGGAGCTGATGGCGTAGG, or GTTGGAGCTGCTGGCGTAGG.

Molecules complementary to a DNA sequence encoding a mutant K-ras protein which contains a single base pair mutation in the codon encoding the amino acid at position 61 have also been synthesized. The nucleotide sequence of these molecules comprises ACAGCAGGTGAAGAGGAGTA, ACAGCAGGTAAAGAGGAGTA, ACAGCAGGTCCAGAGGAGTA, ACAGCAGGTCTAGAGGAGTA, ACAGCAGGTCGAGAGGAGTA, ACAGCAGGTCATGAGGAGTA, or ACAGCAGGTCACGAGGAGTA.

A different embodiment of the invention concerns molecules useful as probes for altered H-ras genes. Molecules complementary to a DNA sequence encoding a mutant H-ras protein which contains a single base pair mutation in the codon encoding the amino acid at position 12 have been produced. The nucleotide sequence of these molecules comprises GTGGGCGCCAGCGGTGTGGG, GTGGGCGCCTGCGGTGTGGG, GTGGGCGCCCGCGGTGTGGG, GTGGGCGCCGACGGTGTGGG, GTGGGCGCCGTCGGTGTGGG, or GTGGGCGCCGCCGGTGTGGG.

Molecules complementary to a DNA sequence encoding a mutant H-ras protein which contains a single base pair mutation in the codon encoding the amino acid at position 61 have been produced. The nucleotide sequence of these molecules comprises ACCGCCGGCGAGGAGGAGTA, ACCGCCGGCAAGGAGGAGTA, ACCGCCGGCCTGGAGGAGTA, ACCGCCGGCCGGGAGGAGTA, ACCGCCGGCCCGGAGGAGTA, ACCGCCGG-CCATGAGGAGTA, or ACCGCCGGCCACGAG-GAGTA.

It is known to those of ordinary skill in the art that DNA sequences complementary to those listed above could also be used in the methods of this invention. One skilled in the art would also know that RNA sequences or corresponding to the above DNA complementary sequences could also be used.

The molecules of this invention may be labeled with detectable moieties such as radioactive, fluorescent or enzymatic markers and used in methods for detecting altered oncogenes which contain single-base pair mutations in specific codons.

The methods of detecting an activated ras gene containing a single-base mutation in a codon encoding an amino acid at a specific position involves cleaving a human subject's genomic DNA with an appropriate restriction enzyme or enzymes under suitable conditions to produce DNA fragments. The resulting fragments are then separated to obtain single-stranded DNA molecules. The restriction fragments can be separated by methods such as gel electrophoresis or column chromatography. The DNA molecules can then be denatured in the gel to obtain single-stranded DNA molecules and then may be neutralized in the gel and the gel dried down. Alternatively the molecules may be transferred to a solid support such as a nitrocellulose filter. The single-stranded DNA molecules in the gel or on a filter may then be contacted with the labeled DNA molecules of the invention under suitable conditions permitting hybridization of complementary molecules. The hybridized molecules are subsequently treated under suitable conditions permitting only fully complementary molecules to remain hybridized and causing imperfectly hybridized molecules to separate. The presence of the fully hybridized molecules and thereby the single-base mutation in the activated -ras gene are then detected. Suitable conditions and methods for restriction enzyme cleavage, gel electrophoresis, hybridization and treatment of the hybridized molecules are described in the First Second Third and Fourth Series of Experiments.

Alternatively the mutations can be detected in the RNA of human tissues. The RNA is isolated from the tissue and separated using methods known to those of ordinary skill in the art, e.g. gel electrophoresis. The RNA may then be transferred to a solid support such as a nitrocellulose filter or alternatively immobilized by drying the gel. The RNA molecules in the gel or on the filter may then be contacted with the labeled DNA or RNA molecules of the invention under suitable conditions permitting the hybridization of complementary molecules. Alternately, hybridization may be performed directly in solution. The hybridized molecules are subsequently treated under suitable conditions permitting only fully complementary molecules to remain hybridized and causing imperfectly hybridized molecules to separate. The presence of the fully hybridized molecules and thereby the single-base pair mutations in the activated ras gene are then detected.

By using the molecules and methods of this invention it is possible to detect altered N-ras, K-ras and H-ras oncogenes with single-base pair mutations at in the codons encoding amino acids at positions 12, 13 and 61.

A specific embodiment of the invention concerns a method of diagnosing acute leukemia. Certain types of acute myeloid leukemia maybe associated with an activated N-ras gene containing a single-base mutation in the codon encoding the amino acid at position 13. The methods of diagnosis involve using the DNA molecules of this invention which are complementary or identical to a nucleotide sequence encoding mutant protein which contains a single-base pair mutation in the codon encoding the amino acid at position 13 in the methods of the invention as described above and in the First and Second Series of Experiments.

A specific embodiment of the invention concerns a method of detecting an activated ras gene which contains a single-base mutation in the codon encoding the amino acid by detecting the altered ras protein product of the mutated gene i.e. N-ras position 13. The method comprises contacting a sample containing the altered ras protein with a monoclonal antibody labeled with a detectable moiety under suitable conditions permitting the formation of an antibody-antigen complex, the antibody being specific for an antigenic site which comprises the amino acid encoded by the codon containing the single-base mutation. The unbound labeled antibody is separated from the labeled antibody-antigen complex. The presence of the labeled antibody-antigen complex is then detected and thus the presence of the altered protein product of the mutated ras oncogene is detected.

FIRST SERIES OF EXPERIMENTS

Materials and Methods
Cell line and DNA

MOLT-4 was obtained from D. Valerio, HL60 from H. Janssen (Netherlands Cancer Institute), HT1080 and RD301 from Dr. A. Hall (London). Genomic DNAs from lines K562 and Rc-2a were gifts from Dr. G. Grosveld (Rotterdam) and H. Janssen, respectively. Plasmids pAT8.8 (containing part of the gene from HT1080) (25) and pSVN-ras (containing the N-ras gene of HL60 under control of the SV40 early promoter) were provided by Dr. A. Hall (London) and Dr. R. A. Weinberg (MIT), respectively, alpha-$^{32}$P dATP (specific activity 3000 Ci/mmole) was obtained from Amersham (U.K.)

Synthetic oligonucleotides

The oligomers were synthesized by the solid phase triester method as described (38). The 8-mer primer was synthesized with a 5'-terminal phosphate group.

Labeling of oligomers $^{32}$P-labeled oligomer probes were synthesized on 20-mer templates corresponding to the antisense sequence of the N-ras gene by enzymatic extension of hybridized 8-mers (39). The reaction was in 10 microliters containing 6 mM Tris-HCl (pH 7.6), 6 mM MgCl, 6 mM 8-mercaptoethanol, 50 mM NaCl, 20 uCi alpha-$^{32}$P dATP, 100 micromols of each of the other dNTPs, 30 nanograms template, 10 nanograms primer and 3 units DNA polymerase I (large subunit) at 0° C. for 1 hour. The reaction was stopped by the addition of 10 microliters formamide and the mixture was loaded onto a 10% polyacrylamide-7M urea sequence gel. Due to the 5' phosphate groups on the elongated strand, it can be separated from the unlabeled template on a 10% polyacrylamid-7M urea gel. The labeled oligomer was visualized by autoradiography, the excised band was eluted in 500 microliters 1 M EDTA and the eluate was used directly for hybridization. The $^{32}$P-labeled oligomers have a specific activity of about $6 \times 10^9$ dpm/microgram.

Acarose gel electrophoresis and direct gel hybridization

Agarose gel electrophoresis and direct-gel hybridization were essentially as described by Studencki and Wallace (39). The DNA digests were electrophoresed in 0.5 cm thick 0.5% agarose gels. The gels were stained with ethidium bromide and photographed under UV-light. Subsequently, The DNA was denatured in situ in 0.4 M NaOH, 0.8 M NaCl (30 minutes at room temperature) and neutralized in 0.5 M Tris-HCl (pH 7.2), 1.5 M NaCl at 0° C. for 30 minutes. Gels were dried on to Whatman 3 MM paper using a Biorad geldryer. The dried gel was wetted with distilled water to remove the Whatman 3 MM paper and sealed in plastic bags for hybridization. Hybridization took place in 5 ml of 5×SSPE (1×SSPE =10 mM sodium phosphate pH 7.0, 0.18 M NaCl and 1 mM EDTA), 0.3% sodium dodecylsulfate containing 10 micrograms/ml sonicated, denatured E. coli carrier DNA for 16 hours at 50° C. Hybridized gels were washed as follows twice in 2×SSPE, 0.1% sodium dodecylsulfate (30 minutes) at room temperature, once in 5×SSPE, 0.1% sodium dodecylsulfate at 52° C. (15 minutes), and once in the same solution at 59° C. for 5 minutes. Gel membranes were covered with Saran wrap and autoradiographed at −70° C. for 4 days using intensifying screens.

Results

Principle of the method

To screen for mutations in codon 61 of the human N-ras gene we have synthesized four different groups of 20-mers (FIG. 1). The first 20-mer (N61-I) has a sequence identical to a 20-long stretch covering the 61st codon (CAA) of the normal N-ras gene. N61-II is a mixture of three 20-mers identical to N61-I except that the position of the first nucleotide of codon 61 the wild-type C has been replaced by A, G or T. As a consequence this group of oligomers can only form an imperfect hybrid with the normal N-ras gene. However, when codon 61 is mutated in its first position, one of the 20-mers of the N61-II group will form a complete match with the mutated gene. Similarly, in N61-II G, T and C substitute for the wild-type second base of the codon. Finally, the two 20-mers of N61-IV have T and C instead of A as the third nucleotide of the codon (substitution of G gives rise to a silent mutation). The oligonucleotide probes used in this study had the sense orientation and were of high specific activity. To attain the latter, we prepared anti-sense 20-mers and a sense 8-mer (complementary to the 3' end of the 20-mers) by chemical synthesis. The label was introduced by incubating this template-primer complex with alpha-$^{32}$P dNTPs and DNA polymerase I (large subunit). The 8-mer primer carried a 5'-terminal phosphate group which enabled us to separate the labeled oligomer from the unphosphorylated template on a polyacrylamide-urea gel. Hybridization of the labeled oligomer probes to plasmid DNA or genomic DNA was performed in a dried agarose gel as described by Schinnick et al. (40) and Studencki and Wallace (39). To that end, DNA was digested, fractionated on a 0.5% agarose gel and denatured in situ, after which the gel was dried. The dried gel membrane was wetted in distilled water and subsequently hybridized with the labeled oligomers. According to Studencki and Wallace this procedure allows the detection of a single gene copy in a relatively small amount of genomic DNA (1–5 micrograms) (39).

To determine the melting temperature of a fully matched hybrid and of a one-basepair mismatched hybrid between one of the 20-mers and the gene, the labeled oligmer probes were hybridized to plasmid DNAs containing a mutation in codon 61 of the N-ras gene. These plasmids, pAT8.8 and pSVN-ras contain parts of the activated genes from a secondary NIH/3T3 cell transfectant of the fibrosarcoma cell line HT1080 (25; $CAA_{61}$-- AAA;13) or from a tertiary transfectant of the promyelytic cell line HL60 (21; $CAA_{61}$-CTA); respectively. In 5×SSPE, the melting temperature for a fully matched hybrid was 61°–62° C., and for a hybrid with a one-basepair mismatch 55°–56° C. We found that hybridization at 50° C. and a final wash at 59° C. were suitable to specifically detect a fully matched hybrid. A mixture of pAT8.8 and pSVN-ras digested with was hybridized to the oligomers N61-I, N61-II, N61-III and N61-IV. A 4.4-bp PstI-fragment from pAT8.8 containing codon 61 with a mutation of the first nucleotide hybridizes only with N61-II which implies that a fully matched hybrid is possible with one of the oligomers present in group N61-II. A rasI-fragment of 2.8 kb from pSVN-ras where codon 61 has a mutation at the second position hybridizes only with N61-III. None of the other oligomer probes hybridizes to the two fragments. This shows that our conditions are specific to detect only fully matched hybrids. The amount of plasmid DNA used (10 and 0.5 hybrid genome copies) furthermore shows that we can detect a single genome copy.

Hybridization to genomic DNA

To test whether we can detect N-ras gene mutations in genomic DNA we have analyzed DNA isolated from both HT1080 and HL60 cells. In addition, we have analyzed DNA derived from four other cells lines three of which have been shown to contain an activated N-ras gene by the 3T3 cell assay: the T-ALL cell line MOLT-4 (27), the AMMoL cell line Rc-2a and the rhabdomyosarcoma cell line RD301 (25). The CML cell line K562 has not been reported to contain an activated ras gene. The DNAs were digested with rasI which generates a 3.6-kb fragment containing codon 61 of the N-ras gene and treated as described in Materials and Methods.

The labeled oligomer probe N61-I hybridizes to a 3.6-kb band in the DNA digests of each of the cell lines showing that all six cell lines contain a normal allele. Only DNA from HT1080 cells hybridizes with N61-II, and only DNA from HL60 cells hybridizes specifically with N61-III. Other hybridizing bands in the HL60 DNA digest are a reproducible background of unknown origin. N61-IV only hybridizes to RD301 DNA showing that this cell line has a mutation in the third position of the 6lst codon. This implies that in the protein of RD301 the normal glutamine (CAA is replaced by histidine (CAC or CAT). From these results we conclude that genomic DNA of both HT1080 and HL60 contains a mutation in the gene at a similar position as found in the isolated genes from NIH 3T3 cell transfectants (the plasmids pAT8.8 (25) and pSVNras (28), respectively). Furthermore, we conclude that in the three cell lines containing a mutated N-ras gene a normal N-ras allele is also present.

Our Oligomers failed to detect a mutation in codon 61 of the N-ras gene of the MOLT-4 cell line and the Rc-2a cell line which both have been reported to have an activated N-ras gene. In these cases the mutation may be in codon 12 as recently found for the human teratocarcinoma cell line PA1 (10). By using mutation specific oligomer probes for mutations in N-ras codon 12 we found that MOLT-4 DNA contains a mutation at the first nucleotide of this codon.

Discussion

We have used synthetic oligonucleotides to detect mutations in codon 61 of the human N-ras gene. We found such mutations in the genomic DNAs of HT1080, HL60 and RD301 at the three possible codon positions. In HT1080 the first nucleotide of codon 61 is mutated and in HL60 the second codon position is mutated. This confirms the results obtained through sequence analysis of activated N-ras genes isolated from 3T3 cells transformed by DNA from these two cell lines (14; J. M. Cunningham and R. A. Weinberg, pers. comm.). In RD301 the third nucleotide is mutated (from A to C or T), which implies that the normal glutamine at position 61 is replaced by histidine. Furthermore, we found that in these three cell lines, in addition to a mutated N-ras allele, a normal allele is present, showing the dominant character of the mutations. The dominant character was already suggested by the ability of the mutated genes to transform NIH/3T3 cells (25, 41). Similarly, both a normal and an affected K-ras gene are present in the lung carcinoma cell line Calu-1 (9). On the other hand, several cell lines have been reported to contain only the mutated allele of an activated ras gene: Hras in the bladder carcinoma cell line T24 (42) and Kras in the colon carcinoma SW480 (8), the lung carcinoma A2182 and the bladder carcinoma A1698 (9).

The use of synthetic oligonucleotides for the detection of mutations in the family of oncogenes may have considerable advantages compared to what is as yet the most feasible alternative, the 3T3 transfection assay. Firstly, the oligonucleotide assay is performed directly on the genomic DNA avoiding the possibility of mutations introduced during the transfection procedure (41). Secondly, it detects both the mutated and the normal alleles. This opens the possibility of discriminating whether a mutation is present in one or in both alleles as discussed above. Furthermore, for those cases where both an activation and an amplification of a particular ras gene have been found (43) it can be detected whether the normal or the mutated allele has been amplified. Answers to those questions may tell whether the ratio between affected and normal alleles plays a role in the tumorigenic properties of a cell. Thirdly, its sensitivity does not depend on so called "weakly transforming alleles" (18) and may be difficult to detect in the 3T3 cell assay. A final advantage of the method is its relative rapidity and easiness. It will allow the screening of larger numbers of tumor tissues for activated ras genes to get a clearer insight into the importance of those activations for in vivo tumorigenesis and tumor progression. The only presently available approach with demonstrated utility for detection of point mutations in members of the ras oncogene family involves assaying for those point mutations that result in changes in cleavage sites for particular restriction endonucleases. However, this approach is limited to only a few very specific point mutations (44). Thus far, our knowledge of the role of activated ras genes in these processes is only limited, especially since most experiments have been done with established cell lines which could have acquired an activated ras gene after their isolation (10).

SECOND SERIES OF EXPERIMENTS

Materials and Methods

Synthesis of 20-mer probes

The N12 and N13 probes were synthesized using a complementary chemically synthesized 20-mer and an 8-mer primer complementary to the 3' end of the 20-mer. This primer-template complex was incubated with alpha-$^{32}$P-dCTP (3000 Ci/mMol, Amersham, U.K.), cold dGTP, dATP and TTP and DNA polymerase I (Klenow's fragment) as described by Bos et al., (17). The 8-mer primer carried a 5'-terminal phosphate group which enabled us to separate the labeled oligomer from the unphosphorylated template on a polyacrylamide urea gel. The N61 probe was synthesized similarly but now using alpha-$^{32}$P-dATP (see ref. 17). The oligonucleotides were prepared by a phosphotriester approach (35) using a fully automatic synthesizer (Biosearch SAM-I). The sequences of the 20-mer N-ras probes are derived from Taparowski et al. (5).

The synthetic oligomer probes described above were hybridized to genomic DNA of 3T3 cell transfectants of four different human Acute myeloid leukemias. Six Replicate gels of each of the DNAs were electrophoresed. The gels each contained samples of DNA of HL60 and HT1080 as controls, and with the DNAs of the AML transfectants 33T, 49T, 77T and 1T. Each gel was hybridized to different oligomer probes; e.g. I: N61-wt, II: N12-wt, III: N12-p1, IV: N12-p2, V: N13-p1, VI: N13-p2. Phage DNA digested with HindIII was used as a molecular weight marker..

Hybridization occurs essentially as described by Bos et al. (17). 10 micrograms genomic DNA was digested with PstI and electrophoresed on a 0.5% agarose gel. The gels were denatured in 0.4 M NaOH, 0.8 M NaCl, neutralized in 0.5 M Tris.HCL pH 7.2, 1.5 M NaCl and subsequently dried on a geldryer. The dried gel membranes were hybridized at 50° C. with N61-wt, and 53° C. with the other probes in 5×SSPE (1×SSPE=10 mM sodium phosphate pH 7.0, 0.18 M NaCl, 1 mM EDTA) 0.3% sodium dodecyl sulphate and 10 micrograms/ml sonicated E.coli DNA. Hybridized gels were washed in 2×SSPE, 0.1% sodium dodecyl sulphate at room temperature, in 5 times SSPE, 0.1% sodium dodesyl sulphate at 53° C. for 15 minutes and finally in the same solution at either 59° C. (for N61-wt) or 63° C. for the N12/13 probes for 5 minutes. Gel membranes were autoradiographed for 2-4 days using intensifying screens.

Hybridization of the separated N13-p2 oligomer probes to genomic DNAs of the AML transfectants was also performed. Each of the three Electrophoresed gels contained Pst I digested DNAs of MOLT4 as control, and the DNAs of AML 33T, 49T, 77T and 1T. The gels were separately hybridized to I: N13-p2/a (TTCCCAACATCACCTGCTCC), to II: N13-p2b (TTCCCAACAACACCTGCTCC) and to III: N13-p2/c (TTCCCAACAGCACCTGCTCC). This plasmid contains 8.8 kb fragment of the activated N-ras gene from HT1080 (CAA$_{61}$-- AAA; 25).

The three members of oligomers N13-p2 were separated on a 20% polyacrylamide gel (mono: bis=62.5:1) in ½× TBE (1×TBE 90 mM Tris, 90 mM boric acid, 2.5 EDTA). To get rid of contamination the isolated oligomers were further purified by electrophoresis on cellulose acetate strips in 7 M urea, 5% acetic acid, 5 mM EDTA pH 3.5 at 5000 V. The fragments were eluted in 1 mM EDTA and used directly for hybridization. The sequence of each oligomer was determined by synthesizing N13-p2 with an end-labeled primer and cold dNTPS. This end-labeled probe was separated into the three members of N13-p2 and sequenced according to Maxam and Gilbert. Gel separation and hybridization was as described above.

Hybridization of N13-p2 and N12-wt oligomer probes to separate replicate gels of genomic DNA of isolated blast cells of AML patient 33, 49 and 1 and to genomic DNA of blood cells from AML patient 33 after remission (REM33) was also performed. Gel separation and hybridization were as described above.

To examine whether any of the tumors that arose in nude mice resulted from the acquisition of a human ras oncogene, DNA prepared from the tumors was analysed by Southern blotting with probes for N-ras, H-ras and K-ras. It was found that DNA prepared from each of the primary transfectants from the four AML DNAs detected by in vivo selection and the one detected by the focus assay contained the human N-ras gene. In many transfectants the human N-ras gene was amplified 20-30 fold. There was no evidence for transfer of any of the other ras oncogenes.

Mutation at codon 13 in altered N-ras genes

We have analyzed the transfected N-ras genes in the NIH 3T3 transfectants derived from AML DNAs we used synthetic 20-mer oligonucleotide probes. Using these probes we are able to detect single basepair substitutions in the N-ras gene based on the fact that a fully-matched hybrid between the oligomer and genomic DNA is more stable than a one-base-pair-mismatched hybrid (24). For the positive detection of mutations we have synthesized groups of oligomers varying at one position in a codon (N12-p1, N12-p2 etc. FIG. 2). One oligomer of each group will then hybridize to form a fully matched hybrid to each of the possible mutations in a basepair. For example the oligomer group N12-p2 consists of 3 oligomers one of which will form a fully-matched hybrid with an N-ras gene mutated at the second base of codon When PstI-digested DNA from 4 AML transfectants (33T, 49T, 77T, 1T) was hybridized to the probe corresponding to the sequence of the normal N-ras gene around codon 61 (N61-wt) and washed under conditions in which only a fully-matched hybrid is stable, a strongly hybridizing signal was seen. In some transfectants (49T, 33T) the signal was very intense showing that the genes were highly amplified. No hybridization was seen with the oligomer groups corresponding to mutations at position 61 indicating that none of the N-ras genes in the transfectants contained mutations at codon 61. In contrast, the oligomer corresponding to the normal sequence of the N-ras gene at codon 12 (N12-wt) failed to form a fully-matched hybrid with any of the AML transfectant DNAs. However, when the DNAs were hybridized with the groups of probes corresponding to mutations at each of the basepairs of codon 12 (N12-p1, N12-p2) fully-matched hybrids were not detected either. The absence of fully-matched hybrids with either normal or mutant probes led us to investigate whether any mutations occurred in the sequence surrounding codon 12. Recently, Fasano et (18) have shown by vitro mutagenesis that mutations in codon 13 (glycine) can lead to transforming activity of the c-H-ras-1 gene. We therefore analyzed the transfectant DNAs by hybridization with probes (N13-p1, N13-p2) that could recognize mutations at the first o second position of codon 13. The oligomer group N13-p2 hybridizes with each of the AML transfectant DNAs. Those transfectants with the highest copy number of the N-ras gene showed the greatest signal with the N13-p2 probe and no hybridization was detected to control DNAs with the wild type sequence. Thus, the N13-p2 probe forms a fully-matched hybrid with the AML transfectant DNAs. No hybridization was detected with the N13-p1 probe to the transfectant or control DNAs. Therefore the transfectant DNAs contain N-ras genes with a mutation at the second position of codon 13. We found that the N-ras gene in transfectant DNA of AML 73 also hybridizes with the N13-p2 probe and thus contains a mutation at the same position.

Mutation at glycine 13 to valine or aspartic acid

The use of mixed oligonucleotide probes allows the detection of the position of a mutation in a codon rather than establishing the precise mutant sequence. In order to analyze the exact nature of the mutations present in the N-ras gene of the AML transfectants we hybridized the DNAs to the individual oligonucleotide probes corresponding to the three possible mutations at the second position of codon 13. To prepare these individual probes the labeled oligonucleotides of group N13-p2 were electrophoresed on a polyacrylamide gel, the individual bands excised and the separated oligomers further purified by electrophoresis on cellulose acetate strips. To identify the separated oligomers they were sequenced as described in the Materials and Methods section. It was found that the slowest running oligomer, on the polyacrylamide gel N13-p2/a, had the sequence TTCCCAACATCACCTGCTCC and thus identifies a GAT codon 13 (aspartic acid) in a fully-matched hybrid.

The second oligomer N13-p2/b identifies a GTT codon (valine), while the third and fastest running oligomer N13-p2/c identifies a GCT codon (alanine). The separated oligonucleotide probes were then hybridized to PstI-digested DNA from four AML transfectants. Oligomer N13-p2/a forms a fully matched hybrid with DNA of transfectants from AML 1 and 33, while oligomer N13-p2/b forms a fully matched hybrid with DNAs from transfectants of AML 49 and 77. No hybridization was Seen with the probe N13-p2/c. Furthermore no hybridization was observed with the separated oligomers to the control MOLT4 DNA. From these results we conclude that the gene in transfectants of AML 1 and 33 DNA contains a GAT codon 13 substituting aspartic acid for glycine, while the transfectants from AML 49, 73 and 77 contain a GTT codon 13 encoding valine. Recently, we found that AML 73 hybridized specifically with N13-p2/b and thus contain a valine at position 13. There is no apparent correlation between the classification of the AMLs and the amino acid substitution: AMLs 1 and 33 (Asp) were classified on the FAB scheme as M4 and M1, respectively whereas AMLs 49 and 77 (Val) were classified as M5 and M4, respectively.

Presence of altered N-ras genes in DNA from leukemic cells and absence from a remission.

To exclude the possibility that the mutations at position 13 were acquired during transfection and selection for transformed cells the DNA from three leukemias was analyzed. DNA was digested with PstI, electrophoresed on an agarose gel and hybridized in situ to the oligonucleotide probes N13-wt and N13-2. Hybridization of the gel to the mutant specific N13-p2 oligomer group showed that all three AML DNAs hybridized. Thus the DNAs from these original leukemic cells also contains the mutation at codon 13, ruling out the possibility that their mutations had arisen as a result of experimental manipulation.

The availability of DNA prepared from the peripheral blood of one patient who was in remission (REM33) allowed us to investigate whether the codon 13 change was present in normal cells. REM33 DNA did not hybridize with the N13-p2 mutant specific probes. As a control we rehybridized the gel with the N12-wt probe. A signal was obtained when the normal sequence probe hybridized to REM33 DNA. Therefore, we conclude that this DNA, and thus the normal tissues of the patient, do not contain an altered gene hybridizing with N13-p2. The altered N-ras gene in this patient therefore has arisen by somatic mutation. Hybridization with the normal sequence probe was also obtained with the three DNAs from leukemias but we do not know whether this is due to the leukemic cells being heterozygous for the normal and mutant N-ras genes or to the presence of normal cells in the leukemic sample. However, the high white blood cell counts of the leukemic samples ($54-140 \times 10^9$ WBC/liter) coupled with the high proportion of cells with blast morphology (95-100%) makes it likely that the hybridization signal with the N12-wt probe is a result of the leukemic cells containing both a normal and a mutant N-ras gene.

Discussion

We have found that a high percentage of DNAs isolated patients with Acute myeloid leukemia contain altered N-ras genes. These activated oncogenes have also been detected in three other samples of AML cells from patients (27-29) and in three AML cell lines HL60 (28), Rc2a and KG-1. Why there should be a bias towards activation of N-ras genes in these leukemias is not clear, but it is also noteworthy that in cell lines of Acute lymphoblastic leukemia N-ras normally appears to be the activated ras oncogene (27, 30). N-ras genes may be critically involved in the control of proliferation and differentiation of cells in the haemapoietic lineage. Alteration of this gene may then lead to the malignant state of the cells. The activation of the same ras oncogene in multiple tumors is reminiscent of findings that there is a reproducible pattern of gene activation in tumors induced by the same carcinogenic agent (31-33). Therefore, it may be that a specific carcinogenic agent is responsible for these N-ras activations.

Unlike previously described examples of ras gene activations (3-17) we have not found mutations in codon 12 or 61. Instead we have observed that mutations occur in codon 13, resulting in a replacement of glycine by either valine or aspartic acid. Although mutation at codon 12 has been observed in one AML (34) the question remains why we observe frequent mutations at codon 1 Clearly, there must be a very precise constraint to this type of mutation. This constraint may arise from the mechanism of mutation or, more likely, may reflect selection for the type of alteration in the p21 protein that is transforming in myeloid cells. One indication that the selection may occur at the protein level is our finding that the genes with a mutation at codon 13 are rather inefficient in inducing focus formation, suggesting that mutations that are strongly transforming for NIH 3T3 cells might be lethal to myeloid cells. It is also possible, however, that mutations that are poorly transforming in the fibroblastic cells may have a more pronounced effect in cells of the myeloid lineage. However, until we have examined many other malignancies, the possibility must be envisaged that codon 13 changes are not specific to AML and are found often in other tumors. Since codon 13 changes may have previously gone undetected the level of ras gene involvement in human tumors may be higher than 10-30% previously found.

Our observations that a high proportion of AMLs we have examined contain an altered N-ras gene with mutations at codon 13 suggest that the activation of the N-ras gene is an essential step in the causation of these AMLs. However, it is unlikely that the activation of the N-ras oncogene is the only step involved in the genesis of AML, since much evidence favours the argument that changes to more than one gene are involved in neoplastic transformation (reviewed in reference 1). Furthermore, specific chromosome translocations and other aberrations are associated with AML (36). These chromosome aberrations occur at sites distinct from the lcen-lp21 chromosomal site of (37) and separate aberrations are found in the different subgroups of AML. For example a translocation, t(8;21), is found in AML M2 and an inversion of chromosome 16, inv16, in AML M4 with increased eosinophils (reviewed in reference 36). In contrast, we have found activation of N-ras in samples of AML from four different subgroups (M1, M2, M4 and M5); thus the activation of N-ras appears to be affecting a process which is essential to all cells in the myeloid lineage, whereas the chromosome aberrations appear to affect genes whose activities are more limited.

For the analysis of the N-ras mutations we have used a set of specific oligonucleotide probes. This assay system is not only powerful in the detection of mutations in transfectant DNAs but also in the detection of specific mutations in tumor DNA. This assay system provides the opportunity to analyze a large number of AML DNAs to get more precise insight into the occurrence of different ras gene mutations in this leukemia.

THIRD SERIES OF EXPERIMENTS

Detection of H-ras and K-ras mutations

DNA of various cell lines containing activated K-ras or H-ras genes were analysed for the presence of a mutation by mutation-specific oligomer probes. We have analyzed the following human cell lines and using the methods described in the first and second series of experiments we have identified point mutations at the positions in parentheses that follow:

| | | |
|---|---|---|
| gastric carcinoma | GAS 431 | (K 12-1) |
| colon carcinoma | SW 480 | (K 12-2) |
| ovarium carcinoma | | (K 12-1) |
| lung carcinoma | LX-1 | (K 12-2) |
| bladder carcinoma | T24 | (H 12-2) |

The position of the mutation is within the parentheses.

SW 480, LX-1 and T24 were obtained form R. Weinberg (Cambridge MA); Ovarium carcinoma was obtained from P. Schrier and GAS 431 was obtained from C. Marshall.

FOURTH SERIES OF EXPERIMENTS

Use of labeled RNA probes to detect single base pair mutations

RNA specific probes may be made in a similar way as the DNA probes using a synthetic DNA oligomer as a template and a small RNA primer. This primer is extended by RNA polymerase in the presence of ribonucleotide triphosphates. Alternative RNA specific probes may be made by cloning the DNA oligomer template into a vector just downstream a transcription promoter. After linearization of the vector just downstream of the inserted oligomer the RNA probes can be synthesized using a promoter specific RNA polymerase and ribonucleotide triphosphates.

Using labeled RNA probes we have found that we can specifically detect the N-ras 61 mutation in the human cell line HT 1080 (N-ras 61-1).

References

1. Land, H., Parada, L. F. and Weinberg, R. A., Science 222, 771-778 (1983). 2. Cooper, G. M., Science 218, 801-806 (1982).
3. Tabin, C. J., Bradley, S. M., Bargmann, C. I., Weinberg, R. A., Papageorge, A. G., Scolnick, E. M., Dhar, R., Lowy, D. R. and Chang, E. H., Nature 300, 143-149 (1982).
4. Reddy, E. P., Reynolds, R. K., Santos, E. and Barbacid, M., Nature 300, 149-152 (1982).
5. Taparowsky, E., Suard, Y., Fasano, O., Shimizu, K., Goldfarb, M. and Wigler, M., Nature 300, 762-765 (19S2).
6. Yuasa, Y., Srivastava, S. K., Dunn, C. Y., Rhim, J. S., Reddy, E. P. and Aaronson, S. A., Nature 303, 775-779 (1983).
7. Shimizu, K., Birnbaum, D., Ruley, M. A., Fasano, O., Suard, Y., Edlund, L., Taparowsky, E., Goldfarb, M. and Wigler, M., Nature 304, 497-500 (1983).
8. Capon, D. J., Seeburg, P. H., McGrath, J. P., Hayflick, J. S., Edman, U., Levinson, A. D. and Goeddel, D. V., Nature 304, 507-513 (1983).
9. Santos, E., Martin-Zanca, D., Reddy, E. P., Pierotti, M. A., Della Porta, G. and Barbacid, M., Science 223, 661-664 (1984).
10. Nakano, H., Yamamoto, F., Neville, C., Evans, D., Mizuno, T. and Perucho, M , Proc. Natl. Acad. Sci. USA (81) 71-75 (1984).
11. Tainsky, M. A., Cooper, C. S., Giovanella, B. C. and Vande Woude G. F., Science 223, 643-645 (1984).
12. Taparowsky, E. Shimizu, K., Goldfarb, M. and Wigler, M., Cell 34, 581-586 (1983).
13. Brown, R., Marshall, C. J., Pennie, S. G. and Hall, A., EMBO J. 3, 1321-1326 (1984).
14. Kraus, M. H., Yuasa Y. and Aaronson, S. A., Proc. Natl. Acad. Sci. U.S.A. 81, 5384-5388 (1984).
15. Yuasa, Y., Gol, R. A., Chang, A., Chiu, I. M., Reddy, E. P., Tronick, S. R. and Aaronson, S. A., Proc. Natl. Acad. Sci. U.S.A. 84, 3670-3674 (1984).
16. Fujita, J., Yoshida, 0., Yuasa, Y., Rhim, J. S., Hatanaka, M. and Aaronson, S. A., Nature 309, 464-466 (1984).
17. Bos, J. L., Verlaan-de Vries, M., Janssen, A. M. Veeneman, G. H., van Boom, J. H. and Van der Eb, A. J., Nucl. Acids Res. 12, 9155-9163 (1984).
18. Fasano, 0., Aldrich, T., Tamanoi, F., Taparowski, E., Furth, M. and Wigler, M., Proc. Natl. Acad. Sci. 81; 4008-4012 (1984).
19. Bennet, J. M., Castovsky, D., Daniel, M. T. Flandrin, G., Galton, D. A. G., Gralnick, H. R. and Sultan, C., Brit. J. Haemat. 33, 451-458 (1976).
20. Blair, D. G., Cooper, C. S., Oskafsson, M. K., Eader, L. A. and Vande Woude, G. F., Science 218, 1122-1124 (1982).
21. Seeburg, P. H., Colby, W. W., Capon, D. J., Goeddel, D. V. and Levinson, A. D., Nature 312, 71-74 (1984).
22. Southern, P. J. and Berg, P. J., Mol Appl. Genet. 1, 327-341 (1982).
23. Fasano, 0., Birnbaum, D., Edlund, L., Fogh, J. and Wigler, M., Mol. Cell. Biol. 4, 1695-1705 (1984).
24. Conner, B. J., Reyes, A. A., Morin, C., Itakura, K., Teplitz, R. L. and Wallace, R. B., Proc. Natl. Acad. Sci. USA 80, 278-282 (1983).
25. Hall, A., Marshall, C. J., Spurr, N. K. and Weiss, R. A., Nature 303, 396-400 (1983).
26. Shih, C., Padkym, L.C., Murray, M. and Weinberg, R. A.
27. Eva, A., Tronick, S. R., Gol, R. A., Pierce, J. H. and Aaronson, S. A., Proc. Natl. Acad. Sci. U.S.A. 80, 4926-4930 (1983).
28. Murray, M. J., Cunningham, J. M., Parada, L. F., Dautry, F., Lebowitz, P. and Weinberg, R. A., Cell 33, 749-757 (1983).
29. Gambke, C., Signer, E. and Moroni, C., Nature 307, 476-478 (1984).
30. Souyri, M. and Fleissner, E., Proc. Natl. Acad. Sci. U.S.A. 80, 6676-6679 (1983).
31. Schermer, S., Notario, V., Martin-Zanka, D. and Barbacid, M., Nature 306, 658-661 (1983).
32. Balmain, A. and Pragnell, I. B., Nature 303, 72-74 (1983).
33. Guerrero, I., Calzada, P., Mayer, A. and Pellicer, A., Proc. Natl. Acad. Sci. U.S.A. 81, 202-205 (1984)
34. Moroni, C., Hall, A. and Gambke, C., Proc. Natl. Acad. Sci. U.S.A. (1985) in press.
35. Marugg, J. E., Piel, M., McLaughlin, L. W., Tromp, M., Veeneman, G. H., Van der Marel, G. A. and Van Boom, J. H., Nucl. Acids Res. 12, 8639-8651 (1984).
36. Ellis, R. W., Defeo, D. Shih, T. Y., Gonda, M. A., Young, H. A., Tsuchida, N., Lowy, D. R. and Scolnick, E. M., Nature 291, 506-511 (1981).
37. McGrath, J. P., Capon, D. J., Goeddel, D. V. and Levinson, A. D., Nature 310, 644-649 (1984).
38. Marug, J. E., McLaughlin, L. W., Piel, N., Tromp, M., van der Marck, G. A. and van Boom, J. H., Tetrahedron Lett. 24, 3989-3992 (1983).
39. Studencki, A. B. and Wallace, R. B., DNA 3, 7-15 (1984).
40. Schinnick, T. M., Lund, E., Smithies, O. and Blattner, F. R., Nucl. Acids Res. 2, 1911-1929 (1975).
41. Calos, M. P., Lebkowski, J. S. and Botchan, M. R., Proc. Natl. Acad. Sci. 80, 3015-3019 (1983).
42. Feinberg, A. P., Vogelstein, B., Droller, M. J., Baylin, S. AB. and Nelkin, B. D., Science 220, 1175-1177 (1983).
43. McCoy, M. S., Toole, J. J., Cunningham, J. M., Chang, E. H., Lowy, D. R. and Weinberg, R. A., Nature 302, 79-81 (1983).
44. Zarbl, H., Sukumar, S., Arthur, A. V., Martin-Zanca, D. and Barbacid, M., Nature 315, 382-385 (1985).
45. Guerrero, I., Villasante, A., Corces, V. and Pellicar, A., Science 225, 1159-1162 (1984).

What is claimed is:

1. A molecule useful as a probe for detecting in a gene from a human subject which encodes a mutated N-ras protein, a single base mutation in the codon at position 13 of the N-ras gene, which mutation results in an amino acid being translated and incorporated into the mutated protein which is different from the amino acid translated and incorporated into a nonmutated ras protein comprising a nucleic acid of at least 12 but not more than 43 nucleotides having the formula:, $5'\text{-}B\text{-}Q\text{-}D_3'$ wherein B represents from 0 to about 20 nucleotides having a sequence complementary to a sequence present in the gene which encodes the mutated N-ras protein, the gene sequence to which B is complementary encoding amino acids at the amino terminal side of the amino acid encoded at position 13 of the N-ras gene;

wherein D represents from 0 to about 20 nucleotides having a sequence complementary to a sequence present in the gene which encodes the mutated N ras protein, the gene sequence to which D is complementary encoding amino acids at the carboxyl terminal side of the amino acid at position 13 of the N-ras gene; and wherein Q represents 3 nucleotides having a sequence complementary to the gene sequence which encodes an amino acid at position 13 other than glycine.

2. A nucleic acid molecule which is complementary to the molecule of claim 1.

3. A molecule of claim 1 wherein the codon Q is ACG, ACA, ACT, AGC, AAC or ATC.

4. A molecule of claim 1 wherein the nucleotide sequence of the molecule is TTCCCAACAC-GACCTGCTCC, TTCCCAACACAACCTGCTCC, TTCCCAACACTACCTGCTCC, TTCCCAACAG-CACCTGCTCC, TTCCCAACAACACCTGCTCC, or TTCCCAACATCACCTGCTCC.

5. A molecule of claim I, labeled with a detachable moiety.

6. A molecule of claim 3, labeled with a detachable moiety.

7. A molecule of claim 4, labeled with a detachable moiety.

* * * * *